(12) United States Patent
Gainer et al.

(10) Patent No.: US 8,974,822 B2
(45) Date of Patent: Mar. 10, 2015

(54) ORAL FORMULATIONS OF BIPOLAR TRANS CAROTENOIDS

(75) Inventors: John L. Gainer, Charlottesville, VA (US); Robert Murray, Charlottesville, VA (US)

(73) Assignee: Diffusion Pharmaceuticals LLC, Charlottesville, VA (US)

( * ) Notice: Subject to any disclaimer, the term of this patent is extended or adjusted under 35 U.S.C. 154(b) by 0 days.

(21) Appl. No.: 13/067,469

(22) Filed: Jun. 2, 2011

(65) Prior Publication Data

US 2011/0300213 A1 Dec. 8, 2011

Related U.S. Application Data

(60) Provisional application No. 61/350,804, filed on Jun. 2, 2010.

(51) Int. Cl.

| | |
|---|---|
| *A61P 25/28* | (2006.01) |
| *A61K 9/00* | (2006.01) |
| *A61P 25/00* | (2006.01) |
| *A61P 35/00* | (2006.01) |
| *A61P 11/00* | (2006.01) |
| *A61P 9/12* | (2006.01) |
| *A61K 9/48* | (2006.01) |
| *A61K 31/202* | (2006.01) |
| *A61P 25/16* | (2006.01) |
| *A61P 11/06* | (2006.01) |
| *A61P 9/10* | (2006.01) |
| *A61K 9/28* | (2006.01) |
| *A61K 9/20* | (2006.01) |

(52) U.S. Cl.
CPC ............... *A61K 31/202* (2013.01); *A61K 9/205* (2013.01); *A61K 9/2054* (2013.01); *A61K 9/2866* (2013.01); *A61K 9/4866* (2013.01); *A61K 9/4891* (2013.01)
USPC ............ 424/463; 424/474; 424/400; 514/560

(58) Field of Classification Search
None
See application file for complete search history.

(56) References Cited

U.S. PATENT DOCUMENTS

| | | | |
|---|---|---|---|
| 2,175,843 | A | 10/1939 | Kuhn et al. |
| 2,948,748 | A | 8/1960 | Guex et al. |
| 3,489,806 | A | 1/1970 | Gutmann et al. |
| 3,687,990 | A | 8/1972 | Gutmann et al. |
| 3,853,993 | A | 12/1974 | Gainer |

(Continued)

FOREIGN PATENT DOCUMENTS

| | | |
|---|---|---|
| AU | 2003215396 | 9/2003 |
| CH | 522 572 | 6/1972 |

(Continued)

OTHER PUBLICATIONS

Lang et al., Parkinson's Disease, New England Journal of Medicine, vol. 339, No. 15, 1044-1053 (1998).*

(Continued)

*Primary Examiner* — Peter J Reddig
*Assistant Examiner* — Sarah Chickos
(74) *Attorney, Agent, or Firm* — Nixon & Vanderhye PC

(57) ABSTRACT

The subject invention relates to a variety of formulations of bipolar trans carotenoids including pharmaceutical compositions for oral delivery of a bipolar trans carotenoid comprising i) a bipolar trans carotenoid, ii) a cyclodextrin, and iii) a coating. The invention also relates to preparation of such formulations and their uses.

20 Claims, 12 Drawing Sheets

Mean TSC plasma concentration following administration of 2.9 mg/kg TSC directly to the(●) ileum (*in-situ* dosing) and (○)stomach.

(56) References Cited

U.S. PATENT DOCUMENTS

| | | | |
|---|---|---|---|
| 3,965,261 A | 6/1976 | Gainer | |
| 3,975,519 A | 8/1976 | Gainer | |
| 4,009,270 A | 2/1977 | Gainer, Jr. | |
| 4,038,144 A | 7/1977 | Gainer | |
| 4,046,880 A | 9/1977 | Gainer | |
| 4,070,460 A | 1/1978 | Gainer, Jr. | |
| 4,105,855 A | 8/1978 | Schulz et al. | |
| 4,176,179 A | 11/1979 | Gainer | |
| 4,216,211 A | 8/1980 | Francis | |
| 4,727,064 A | 2/1988 | Pitha | |
| 5,032,613 A | 7/1991 | Watson | |
| 5,424,407 A | 6/1995 | Tanaka et al. | |
| 5,472,946 A | 12/1995 | Peck et al. | |
| 5,817,332 A | 10/1998 | Urtti et al. | |
| 6,060,511 A | 5/2000 | Gainer | |
| 6,150,561 A | 11/2000 | Kreienbühl et al. | |
| 7,145,025 B2 | 12/2006 | Lockwood et al. | |
| 7,446,101 B1 | 11/2008 | Madhavi et al. | |
| 7,759,506 B2 | 7/2010 | Gainer et al. | |
| 8,030,350 B2 * | 10/2011 | Gainer et al. | 514/547 |
| 2002/0065320 A1 | 5/2002 | Messadek | |
| 2003/0072801 A1 | 4/2003 | Curatolo et al. | |
| 2003/0180282 A1 | 9/2003 | Serebruany et al. | |
| 2003/0186931 A1 | 10/2003 | Matsuo et al. | |
| 2004/0014725 A1 | 1/2004 | Gainer et al. | |
| 2004/0109920 A1 | 6/2004 | Reuscher et al. | |
| 2004/0116729 A1 | 6/2004 | Gainer et al. | |
| 2004/0162329 A1 | 8/2004 | Lockwood et al. | |
| 2005/0113372 A1 * | 5/2005 | Lockwood et al. | 514/237.5 |
| 2006/0194973 A1 * | 8/2006 | Gainer et al. | 554/121 |
| 2006/0233877 A1 | 10/2006 | Messadek et al. | |
| 2006/0276372 A1 | 12/2006 | Lockwood et al. | |
| 2006/0281724 A1 * | 12/2006 | Loria | 514/178 |
| 2007/0088248 A1 | 4/2007 | Glenn et al. | |
| 2007/0135521 A1 * | 6/2007 | Okada et al. | 514/547 |
| 2007/0166339 A1 | 7/2007 | Gupta | |
| 2008/0113031 A1 | 5/2008 | Moodley et al. | |
| 2008/0255246 A1 * | 10/2008 | Gainer | 514/763 |
| 2009/0110746 A1 | 4/2009 | Gainer et al. | |
| 2009/0118227 A1 * | 5/2009 | Jouni et al. | 514/54 |
| 2009/0169586 A1 | 7/2009 | Tracton | |
| 2009/0176287 A1 | 7/2009 | Schmidt-Dannert et al. | |

FOREIGN PATENT DOCUMENTS

| | | |
|---|---|---|
| CN | 1215723 | 5/1999 |
| CN | 1215723 A | 5/1999 |
| CN | 1708480 A | 12/2005 |
| CN | 1708480 A | 12/2005 |
| CN | 1997365 A | 7/2007 |
| CN | 101180257 | 5/2008 |
| CN | 101180257 A | 5/2008 |
| EP | 0 612 815 A1 | 8/1994 |
| EP | 0 908 449 | 4/1999 |
| EP | 1 192 947 A1 | 4/2002 |
| GB | 2 353 934 | 3/2001 |
| JP | 45-014114 | 5/1970 |
| JP | 61-254161 | 11/1986 |
| JP | 63-59831 | 3/1988 |
| JP | 63-059831 | 3/1988 |
| JP | 63-222114 | 9/1988 |
| JP | 63-222114 A | 9/1988 |
| JP | 1-238536 | 9/1989 |
| JP | 2-121934 | 5/1990 |
| JP | 05-032531 | 2/1993 |
| JP | 5-32531 | 2/1993 |
| JP | H-09512552 | 12/1997 |
| JP | 10-502388 T | 3/1998 |
| JP | 11029466 | 2/1999 |
| JP | 11-180901 A | 6/1999 |
| JP | 11-180901 | 7/1999 |
| JP | 2000-007570 | 1/2000 |
| JP | 2001-511135 A | 8/2001 |
| JP | 2002-538113 | 11/2002 |
| JP | 2003-26607 A | 1/2003 |
| JP | 2003-201238 | 7/2003 |
| JP | 2005-53841 | 3/2005 |
| JP | 2006-525270 | 11/2006 |
| JP | 2006-342108 | 12/2006 |
| JP | 2006342108 A | 12/2006 |
| JP | 2007-522570 | 8/2007 |
| JP | 2009-274988 | 5/2010 |
| JP | 2010-110185 | 10/2010 |
| RU | 2107496 | 3/1998 |
| RU | 2226096 C1 | 3/2004 |
| RU | 2256446 | 7/2005 |
| RU | 2265434 C2 | 12/2005 |
| WO | WO 92/15544 | 9/1992 |
| WO | WO 9500130 | 1/1995 |
| WO | 98/14183 | 4/1998 |
| WO | WO 98/14183 | 4/1998 |
| WO | WO 98/14183 A1 | 4/1998 |
| WO | WO 9814183 | 4/1998 |
| WO | WO 9814183 A1 | 4/1998 |
| WO | WO 98/32421 | 7/1998 |
| WO | 03/072734 | 9/2003 |
| WO | WO 03/072734 | 9/2003 |
| WO | WO 03/72734 A2 | 9/2003 |
| WO | WO 03/072734 A2 | 9/2003 |
| WO | WO 03/072734 A3 | 9/2003 |
| WO | WO 2004/011423 | 2/2004 |
| WO | 2004/049095 | 6/2004 |
| WO | WO 2004/049095 | 6/2004 |
| WO | WO 2004049095 | 6/2004 |
| WO | WO 2005/028411 | 3/2005 |
| WO | WO 2005/028411 A1 | 3/2005 |
| WO | 2005/120495 | 12/2005 |
| WO | WO 2005/120495 | 12/2005 |
| WO | WO 2005120495 | 12/2005 |
| WO | WO 2006/104610 | 10/2006 |
| WO | WO 2006/104610 A2 | 10/2006 |
| WO | WO 2008/014685 A1 | 2/2008 |
| WO | WO 2008/027687 | 3/2008 |
| WO | WO 2008/102563 A1 | 8/2008 |
| WO | WO 2008/135090 | * 11/2008 |
| WO | WO 2008/136900 | 11/2008 |
| WO | WO 2009/111688 A2 | 9/2009 |
| WO | WO 2011/152869 A1 | 12/2011 |

OTHER PUBLICATIONS

EP Office Action dated Oct. 17, 2011, from European Patent Application No. EP 08742781.1.

English translation of Chinese Patent Office Action issued on Jan. 18, 2012 in Chinese Patent Application No. 200680013663.0 based on PCT/US2006/06422.

Eurasian Patent Office Action (and English translation) dated Nov. 17, 2011.

General Information on Perfluorane. Medline.ru-Biomeditsinskii Zhurnal, 2004, vol. 5, art. 16, pp. 68-69, www.medline.ru/public/art/tom5/art8-perf2.phtm (with English translation).

Abusuev, A.A., Clinical Course of Myocardial Infarction in Treatment with Perfluorane, in Perfluorocarbon Compounds in Experimental and Clinical Medicine, Collected Works of the Russian Scientific Conference, St. Petersburg, 2004, p. 12.

Kichev, G.S., et al, Experience of Using Perfluorane in Treating Critical Conditions of Various Geneses. Medline.ru-Biomeditsinskii Zhurnal, 2004, vol. 5, art. 53, pp. 175-177.

Burukhina, A.N., et al, Experience of Using Perfluorane in Treating Acute Massive Hemorrhage in Obstetric Practice, in Collected Works of the 12th Scientific and Practical Conference of Physicians "Topical Issues in Modern Medicine," Novosibirsk, 2002, Chapter 2, pp. 39-40.

Borisova, I.V., et al, Renal and Neuroprotective Effects of Perfluorane in Induced Toxic Renal Injury in Rats. Medline.ru-Biomeditsinskii Zhkurnal, 2004, vol. 5, art. 16, pp. 136-139.

Office Action dated Mar. 16, 2012 from U.S. Appl. No. 13/137,324.
Office Action dated Dec. 19, 2011 from U.S. Appl. No. 12/801,726.
International Search Report dated Sep. 9, 2011 in PCT/US 11/00997.
Written Opinion dated Sep. 9, 2011 in PCT/US 11/00997.
Office Action dated Sep. 22, 2011 from U.S. Appl. No. 11/790,779.

(56) References Cited

OTHER PUBLICATIONS

Japanese Office Action mailed Oct. 4, 2011, and English translation.
Wirz, R., et al, Helv. Chim. Acta, vol. 43, No. 6, 1960, pp. 1738-1745, (XP008042762).
Wenkert, E., et al, J. Org. Chem., vol. 55, No. 25, 1990, pp. 6203-6214, (XP002317164).
Nihon Butsuri Gakkai Shi, *Journal of the Physical Society of Japan*, 1995, 50(7), p. 555-561, "Structure and Function of Cartenoid in Photosynthetic System."
Eurasian Patent Office Action (English translation) dated Nov. 9, 2011.
Mexican Office Action dated Oct. 20, 2011 (with English translation).
Johnson, et al, *Journal of Pharmaceutical Sciences*, vol. 85, No. 7, 1996, pp. 670-679, "Synergistic effects of chemical enhancers and therapeutic ultrasound on transdermal drug delivery."
New Zealand Examination Report dated Oct. 2011 that issued in the applicant's New Zealand Patent Application No. 595624.
Examination Report dated Apr. 7, 2010 issued by the New Zealand Patent Office in Applicants' corresponding foreign application No. 584433.
Isler, O., et al, Helv. Chim. Acta, vol. 40, No. 5, 1957, pp. 1242-1249, (XP008042920).
Database Caplus, Chemical Abstracts Service, Columbus, Ohio, US; (XP002317165) [JP 63 059831].
Wenkert, E., et al, J. Org. Chem., vol. 55, No. 25, 1990, p. 6203-6214 (XP002317164).
Database Caplus, Chemical Abstracts Service, Columbus, Ohio, US; (XP002317166) [JP 05 032531].
Gibson, T.W., et al, J. Org. Chem., vol. 41, No. 5, 1976, pp. 791-793, (XP002325593).
International Preliminary Report on Patentability (IPRP) (Chapter I) for PCT/US2010/001794, issued Jan. 12, 2012.
European Patent Office Action dated Oct. 31, 2011, from European Patent Application No. EP 06758166.0.
Chinese Office Action issued Jun. 14, 2012, from Chinese Patent Application No. 200880114310.9 that corresponds to PCT/US2008/012440, and its English translation.
Japanese Patent Office Action dated Jul. 10, 2012, from Japanese Patent Application No. 2009-279890 based on PCT/US03/26424, and its English translation.
Helvetica Chemica Acta, 1960, 43(6), p. 1738-1745.
Journal of Organic Chemistry, 1990, 55(25), pp. 6203-6214.
English translation of Japanese Office Action dated Jul. 10, 2012, for applicant's Japanese Patent Application No. 2009-274988 corresponding to PCT/US03/05521 filed Feb. 25, 2003.
Korean Patent Office Action dated Sep. 26, 2012, from Korean Patent Application No. 10-2007-7021197 based on PCT/US2006/006422, and its English translation.
Office Action dated Sep. 6, 2012 from U.S. Appl. No. 13/137,322.
Office Action dated Sep. 18, 2012 from U.S. Appl. No. 13/137,337.
Chinese Patent Office Action dated Jun. 6, 2012, from Chinese Patent Application No. 200880015671.8 based on PCT/US08/004708, and its English translation.
EPO Notice dated Jun. 11, 2012, from European Patent Application No. EP 08742781.1.
Office Action dated Jul. 26, 2012 from U.S. Appl. No. 12/801,726.
European Office Action dated Apr. 25, 2012.
Moelbert, S., et al, Biophysical Chemistry 112, No. 1, (2004) pp. 45-57, "Kosmotropes and chaotropes: modeling preferential exclusion, binding and aggregate stability," XP004610642.
Finney, J., et al, Annals of the New York Academy of Sciences, vol. 141, No. 1, Mar. 15, 1967, pp. 231-241, "Protection of the ischemic heart with DMSO alone or DMSO with hydrogen peroxide."
Mexican Patent Office Action dated Aug. 27, 2012 that corresponds to Applicant's U.S. Appl. No. 12/081,236, filed Apr. 11, 2008. [no translation].
Zheng, S., et al, J. Cardiovasc. Pharmacol, vol. 47, No. 1, Jan. 2006, pp. 70-76, "Crocetin Attenuates Atherosclerosis in Hyperlipidemic Rabbits Through Inhibition of LDL Oxidation." XP009135396.

Supplementary European Search Report dated Oct. 29, 2012 issued by the EPO and Preliminary Opinion.
Lapchak, Paul A., *Brain Research*, vol. 1309, Jan. 14, 2010, pp. 136-145, "Efficacy and safety profile of the carotenoid trans sodium crocetinate administered to rabbits following multiple infarct ischemic strokes: A combination therapy study with tissue plasminogen activator," XP-002686117.
Wang, Y, et al, Society for Neuroscience Abstract Viewer and Itinerary Planner, vol. 38, 2008, "The effect of trans-sodium crocetinate in a model of intracranial hemorrhage," XP009163975.
Chinese Patent Office Action dated May 3, 2012, from Chinese Patent Application No. 03804566.4 based on PCT/US03/05521, and its English translation.
Ladig et al, *J. Am. Chem. Soc.*, 120, 9394-9395 (1998).
International Preliminary Report on Patentability (IPRP) (Chapter I) for PCT/US2011/000997, issued Dec. 13, 2012.
Office Action dated Dec. 24, 2012 from U.S. Appl. No. 13/137,324.
Japanese Office Action (Notice of Reasons for Rejection) dated Jan. 29, 2013, for applicant's Japanese Patent Application No. 2010-503069 corresponding to PCT/US08/004708 filed Apr. 11, 2008, and its English translation.
Chinese Office Action issued Jan. 28, 2013, from Chinese Patent Application No. 200880015671.8 that corresponds to PCT/US2008/004708, and its English translation.
India Office Action (Examination Report) dated Feb. 21, 2013, for applicant's India Patent Application No. 6688/DELNP/2007 corresponding to PCT/US2006/006422 filed Feb. 24, 2006.
Schwieter, U., et al, "Synthesen in der Carotinoid-Reiche 20. Mitteilung Neu Synthesen von Apocarotinoiden," Helvetica Chimica Acta, vol. 1, (1966), pp. 369-390, compound 36 on p. 375, XP-002575142.
Database HCAPLUS on STN, DN 141:388250, Magesh, V. "Studies on the anti-tumor effect of crocetin against benzo(a)pyrene induced lung cancer in Swiss albino mice." XP008117254 Retrieved from STN Databse accession No. (141:388250) & Biomedicine, (Chennai, India) (2003), 23 (3 & 4), 96-99, Abstract.
Japanese Patent Office Action dated Feb. 19, 2013, from applicant's Japanese Patent Application No. 2009-279890 corresponding to PCT/US03/26424 filed Aug. 25, 2003, and its English translation.
Office Action dated Apr. 5, 2013 from U.S. Appl. No. 13/137,322.
Canadian Office Action dated Mar. 26, 2013, for applicant's Canadian Patent Application No. 2,598,882 corresponding to PCT/US06/006422 filed Feb. 24, 2006.
Chinese Patent Office Decision of Rejection dated May 2, 2013 and its English translation, corresponding to PCT/US2006/06422 filed on Feb. 24, 2006.
Laidig, K.E. et al, Altering Diffusivity in Biological Solutions through Modification of Solution Structure and Dynamics, *Journal of the American Chemical Society*, 1998, vol. 120, No. 36, pp. 9394-9395, (XP 002970835).
Extended European Search Report dated Mar. 28, 2013 issued by the EPO and Written Opinion.
Zheng, S., et al, Journal of Cardiovascular Pharmacology, vol. 47, No. 1, Jan. 2006, pp. 70-76, "Crocetin Attenuates Atherosclerosis in Hyperlipidemic Rabbits Through Inhibition of LDL Oxidation." XP009135396.
Israel Office Action dated Apr. 10, 2013, from applicant's Israel Patent Application No. 185460 corresponding to PCT/US06/06422 filed Feb. 24, 2006, and its English translation.
Office Action dated Jun. 12, 2013 from U.S. Appl. No. 12/801,726.
Japanese Office Action dated Jul. 10, 2012, for applicant's Japanese Patent Application No. 2009-274988 corresponding to PCT/US03/05521 filed Feb. 25, 2003, and its English translation.
R. Wirz et al, Helv. Chim. Acta, vol. 43, No. 6, 1738-1745 (1960), XP008042762.
E. Wenkert et al, J. Org. Chem., vol. 55, No. 25, 6203-6214 (1990), XP-002317164.
Japanese Office Action (Notice of Reasons for Rejection) dated Jun. 4, 2013, from applicant's Japanese Patent Application No. 2011-209754 corresponding to PCT/US06/06422 filed Feb. 24, 2006, and its English translation.
Pharmacia, 1991, vol. 27, No. 7, pp. 703-705 (no English translation).

(56) References Cited

OTHER PUBLICATIONS

U.S. Office Action dated Nov. 20, 2013 from U.S. Appl. No. 13/137,337, Gainer et al.
U.S. Office Action dated Dec. 6, 2013 from U.S. Appl. No. 13/137,322, Gainer.
U.S. Office Action dated Jan. 30, 2014 from U.S. Appl. No. 12/801,726, Gainer.
Japanese Office Action (Final Rejection) dated Feb. 4, 2014 from applicant's Japanese Application No. P2011-209754 corresponding to PCT/US06/06422 filed Feb. 24, 2006, and its English translation. Pharmacia. 1991, vol. 27, No. 7, pp. 703-705.
EP Office Action dated Mar. 12, 2014, from applicant's European Patent Application No. EP 12166293.6, corresponding to PCT/US2006/006422 filed Feb. 24, 2006.
Lancrajan, Ioana, et al, *Chemistry and Physics of Lipids*, vol. 112, No. 1, (2001), pp. 1-10, "Carotenoid incorporation into natural membranes from artificial carriers: liposomes and beta-cyclodextrins," XP55044152.
Pfitzner, Inka, et al, *Biochimica et Biophysica Acta*, vol. 1474, No. 2, (2000), pp. 163-168, "Carotenoid:methyl-beta-cyclodextrin formulations: an improved method for supplementation of cultured cells," XP004276552.
Wilkins, E.S., et al, *Cancer Biochem. Biophys.*, vol. 3, (1979), pp. 71-74, "The Effect of Crocetin on the Irradiation of Walker-256: in vitro and in vivo studies," XP008157982.
Rowinsky, Eric K., *Oncology*, vol. 13, No. 10, Supplement No. 5, (Oct. 1999), pp. 61-70, "Novel Radiation Sensitizers Targeting Tissue Hypoxia," XP009044613.
Supplementary (Extended) European Search Report dated Oct. 21, 2013 in European Patent Application No. EP11790107.4 issued from PCT/US2011/000997 filed on Jun. 2, 2011, together with the Opinion.
Lapchak, P.A., *Brain Research*, vol. 1309, Jan. 2010, pp. 136-145, "Efficacy and safety profile of the carotenoid trans sodium crocetinate administered to rabbits following multiple infarct ischemic strokes: A combination therapy study with tissue plasminogen activator," XP-002686117.
Wang, Y., et al, Abstracts of the Annual Meeting of the Society for Neuroscience, Society for Neuroscience, Washington, DC, US, vol. 38, Nov. 15, 2008, "The effect of trans-sodium crocetinate in a modes of intracranial hemorrhage," XP-009163975.
Gainer, J.L., et al, *Pulmonary Pharmacology & Therapeutics*, Academic Press, GB. vol. 18, No. 3, Jun. 1, 2005, pp. 213-216, "The effect of trans sodium crocetinate (TSC) in a rat oleic acid model of acute lung injury," XP004737366.
Chinese Office Action issued Mar. 19, 2014, from Chinese Patent Application No. 200880015671.8 that corresponds to PCT/US2008/004708, and its English translation.
Chinese Office Action issued Mar. 31, 2014, from Chinese Patent Application No. 201210063676.6 that corresponds to PCT/US2003/026524, filed Aug. 25, 2003, and its English translation.
Chinese Search Report dated Mar. 19, 2014 from Chinese Patent Application No. 201210063676.6 that corresponds to PCT/US2003/026524, filed Aug. 25, 2003, and its English translation.
Wenkert, E., et al, *J. Org. Chem.*, vol. 55, No. 25, 1990, pp. 6203-6214 "Polyene Synthesis. Ready Construction of Retinol-Carotene Fragments, . . . Corticrocin." (XP002317164).
Ladig, K.E., et al, *J. Am Chem. Soc.*, vol. 120, pp. 9394-9395 (1998) "Altering Diffusivity in Biological Solutions through Modification of Solution Structure and Dynamics."
Australian Office Action dated Dec. 23, 2011.
Office Action dated Jan. 24, 2012 from U.S. Appl. No. 13/137,322.
Japanese Office Action dated Apr. 22, 2014 from applicant's Japanese Application No. P2010-531078 corresponding to PCT/US08/012440 filed Oct. 31, 2008, and its English translation.
U.S. Office Action dated May 8, 2014 from U.S. Appl. No. 13/507,365, Gainer.
Canadian Office Action dated May 30, 2013, for applicant's Canadian Patent Application No. 2,683,760 corresponding to PCT/US2008/004708 filed Apr. 11, 2008.

Japanese Decision of Rejection dated May 21, 2013, from applicant's Japanese Patent Application No. 2010-110185 corresponding to PCT/US2003/05521 filed Feb. 25, 2003, and its English translation.
Chinese Office Action issued May 6, 2013, from Chinese Patent Application No. 201080027664.7 that corresponds to PCT/US2010/001794, and its English translation.
Chinese Search Report dated Mar. 18, 2013, and its English translation.
Office Action dated Jul. 16, 2013 from U.S. Appl. No. 13/137,324.
Chinese Office Action issued Jul. 9, 2013, from Chinese Patent Application No. 200880114310.9 that corresponds to PCT/US2008/012440, and its English translation.
Chinese Search Report dated Jun. 27, 2013, and its English translation.
Israel Office Action issued Oct. 29, 2013, from Israel Patent Application No. 201438 that corresponds to PCT/US2008/004708, and its English translation.
Chinese Office Action issued Nov. 1, 2013, from Chinese Patent Application No. 201180033875.6 that corresponds to PCT/US2011/000997, and its English translation.
Office Action dated Aug. 22, 2013 from U.S. Appl. No. 13/507,365.
Japanese Office Action (Final Rejection) dated Sep. 10, 2013, from applicant's Japanese Application No. P2009-279890 corresponding to PCT/US03/26424 filed Aug. 25, 2003, and its English translation.
Japanese Office Action (Final Rejection) dated Nov. 26, 2013, from applicant's Japanese Application No. P2010-503069 corresponding to PCT/US08/004708 filed Apr. 11, 2008, and its English translation.
Japanese Office Action (Reasons for Rejection) dated Jun. 18, 2013, in Japanese App. No. 2010531078 (no English translation).
Extended European Search Report dated Nov. 21, 2012 issued by the EPO and Preliminary Opinion.
Lancrajan, I., et al, *Chemistry and Physics of Lipids*, vol. 112, No. 1, Jul. 2001, pp. 1-10, "Carotenoid incorporation into natural membranes from artificial carriers: liposomes and β-cyclodextrins," XP55044152.
Pfitzner, I., et al, *Biochimica et Biophysica Acta*, General Subjects, Elsevier Science Publishers, NL, vol. 1474, No. 2, Apr. 6, 2000, pp. 163-168, "Carotenoid:methyl-β-cyclodextrin formulations: an improved method for supplementation of cultured cells," XP004276552.
Wilkins, E.S., et al, *Cancer Biochem. Biophys*, Gordon and Breach Science Publishers Ltd., vol. 3, 1979, pp. 71-74, "The Effect of Crocetin on the Irradiation of Walker-256: In Vitro and In Vivo Studies," XP008157982.
Rowinsky, E.K., *Oncology*, vol. 10, No. Suppl. 5, Oct. 1999, pp. 61-70, "Novel Radiation Sensitizers Targeting Tissue Hypoxia," XP009044613.
Office Action dated Jan. 4, 2012 from U.S. Appl. No. 13/137,337.
Gainer, John L., "Trans-Sodium Crocetinate for Treating Hypoxia/Ischemia," Expert Opinion on Investigational Drugs, vol. 17, No. 6, 2008, pp. 917-924.
Wang, Y. et al., "The Effect of Trans-Sodium Crocetinate in a Model of Intracranial Hemorrhage," Society for Neuroscience Abstract Viewer and Itinerary Planner, vol. 38, 2008, 2 pp.
Japanese Office Action dated Jun. 24, 2014 issued in Japanese Patent Application No. P2012-516071 and Entlish Translation, 10 pp.
U.S. Office Action dated Jun. 26, 2014 issued in U.S. Appl. No. 13/137,337, 24 pp.
Chinese Office Action dated Jul. 21, 2014 issued in Chinese Patent Application No. 200680013663.0 and English Translation, 9 pp.
Chinese Office Action dated Jul. 24, 2014 issued in Chinese Patent Application No. 200880114310.9 and English Translation, 19 pp.
Chinese Office Action dated Aug. 15, 2014 issued in Chinese Patent Application No. 201080027664.7 and English Translation, 13 pp.
Helvetica Chimica Acta, vol. 43 (6), 1960, pp. 1738-1745.
Japanese Office Action mailed Sep. 9, 2014 issued in Japanese Patent Application No. 2013-197629, 5 pp.
Journal of Organic Chemistry, vol. 55 (25), Dec. 7, 1990, pp. 6203-6214.
Korean Office Action dated Jul. 28, 2014 issued in Korean Patent Application No. 10-2009-7023432 and English Translation, 8 pp.

(56) References Cited

OTHER PUBLICATIONS

Galinski, Erwin A. et al., "The Kosmotropic (Structure-Forming) Effect of Compensatory Solutes," Comp. Biochem. Physiol., vol. 117A, No. 3, Dec. 31, 1997, pp. 357-365.

Laidig, Keith E. et al., "Altering Diffusivity in Biological Solutions through Modification of Solution Structure and Dynamics," Journal of the American Chemical Society, vol. 120, No. 36, pp. 9394-9395.

Lever, M. et al., "Some Ways of Looking at Compensatoroy Kosmotropes and Different Water Environments," Comparative Biochemistry and Physiology Part A, vol. 130, Dec. 31, 2001, pp. 471-486.

Stennett, Amanda K. et al., "*trans*-Sodium Crocetinate and Diffusion Enhancement," The Journal of Physical Chemistry B Letters, vol. 110, Issue 37, Aug. 29, 2006, pp. 18078-18080.

Tong, Linhui, "Cyclodextrins Chemistry: Fundamentals and Application," Science Press, Mar. 2001, pp. 360-364.

United States Office Action dated Sep. 8, 2014 issued in U.S. Appl. No. 12/801,726, 23 pp.

English Translation of Israel Office Action dated May 4, 2014 from applicant's Israel Patent Application No. 185460 corresponding to PCT/US06/06422 filed Feb. 24, 2006.

U.S. Office Action dated Jun. 9, 2014 from U.S. Appl. No. 13/137,324, Gainer et al.

Japanese Office Action dated Sep. 9, 2014 issued in Japanese Patent Application No. P2010-531078 and English translation, 6 pp.

U.S. Office Action dated Oct. 1, 2014 issued in U.S. Appl. No. 13/621,650, 51 pp.

Dec. 8, 2014 Office Action (Reexamination Decision) from the Chinese Patent Office in applicant's Chinese Application corresponding to PCT Application No. PCT/US06/06422 . . . and translation.

Laidig et al article: "Altering Diffusivity in Biological Solutions through Modification of Solution Structure and Dynamics,", pp. 9394-9395, Journal of the American Chemical Society, 1998.

Cyclodextrins Chemistry: Fundamentals and Application, Linhui Tong, Science Press, Mar. 2001, p. 360-364.

Dec. 10, 2014 Office Action from the Australian Patent Office for applicant's Australian application corresponding to PCT Application No. PCT/US2008/012440.

Johnson et al., "Synergistic effects of chemical enhancers and therapeutic ultrasound on transdermal drug delivery", Journal of Pharmaceutical Science.1996; 85(7): 670-679.

Dec. 29, 2014 USPTO Office Action in U.S. Appl. No. 13/507,365.

Dec. 3, 2014 Office Action from the Australian Patent Office for applicant's Australian application corresponding to PCT Application No. PCT/US03/26424.

Dec. 22, 2014 Notice and Office Action from the China Patent Office for applicant's China application corresponding to PCT Application No. PCT/US2011/000997—English translations.

Dec. 8, 2014 USPTO Office Action in U.S. Appl. No. 13/137,324.

Nov. 21, 2014 Office Action from the EPO for applicant's EP Application No. 03818748.0 = based on PCT/US2003/26424.

\* cited by examiner

Figure 1. Mean TSC plasma concentration following administration of 2.9 mg/kg TSC directly to the(●) ileum (*in-situ* dosing) and (○)stomach.

Figure 2: Effect of g-cyclodextrin on TSC absorption in the jejunum of the rat.

Figure 4: Effect of TSC dosage in a TSC-γ-cyclodextrin mixture on Cmax.

ORAL FORMULATIONS OF BIPOLAR TRANS CAROTENOIDS

This application claims priority from U.S. provisional patent application No. 61/350,804, filed on Jun. 2, 2010, the entire contents of which are hereby incorporated by reference.

The subject invention relates to formulations of diffusion enhancing compounds. The compositions of the subject invention typically include a bipolar trans carotenoid, a cyclodextrin and a coating. Included are compositions that are enterically coated with a pH responsive compound for oral delivery.

BACKGROUND OF THE INVENTION

Peroral delivery of therapeutics is generally considered to be the most popular method of drug delivery for patients since this route, in general, increases patient compliance, decreases the number of side effects associated with injections, and provides convenience for the user. Such an administration route is greatly favored for dosing chronically ill patients.

Carotenoids are a class of hydrocarbons consisting of isoprenoid units. The backbone of the molecule consists of conjugated carbon-carbon double and single bonds, and can also have pendant groups. Crocetin and trans sodium crocetinate (TSC) are known to increase the diffusivity of oxygen in aqueous solutions.

U.S. Pat. No. 6,060,511 relates to trans sodium crocetinate (TSC) and its uses. The patent covers various uses of TSC such as improving oxygen diffusivity and treatment of hemorrhagic shock.

U.S. patent application Ser. No. 10/647,132 relates to synthesis methods for making bipolar trans carotenoid salts (BTC) and methods of using them.

U.S. patent application Ser. No. 11/361,054 relates to improved BTC synthesis methods and novel uses of the BTC.

U.S. patent application Ser. No. 12/081,236 relates to the use of bipolar trans carotenoids as a pretreatment and in the treatment of peripheral vascular disease.

U.S. patent application Ser. No. 12/289,713 relates to a new class of therapeutics that enhance small molecule diffusion.

U.S. Provisional Application Ser. No. 61/213,575 relates to the use of diffusion enhancing compounds with thrombolytics.

A variety of bipolar trans carotenoids formulations have been disclosed. See commonly owned application U.S. patent application Ser. No. 10/647,132 and U.S. patent application Ser. No. 11/361,054.

SUMMARY OF THE INVENTION

The pharmaceutical compositions of the subject invention include a diffusion enhancing compound, a cyclodextrin and a coating. The invention also relates to methods of forming a pharmaceutical composition for oral delivery of a bipolar trans carotenoid comprising mixing a bipolar trans carotenoid with a cyclodextrin, adding the mixture to a capsule or making a tablet, and adding coating, advantageously, an enteric coating. Also included in the invention are methods of increasing the diffusivity of oxygen in a mammal and methods of treating a mammal having a disease or condition characterized by hypoxia such as ischemia, cancer, traumatic brain injury, respiratory disease, hemorrhagic shock, cardiovascular disease, multiple organ failure, atherosclerosis, PAD, PVD, myocardial infarction, emphysema, asthma, ALI, ARDS, COPD, hypertension, cerebral edema, papillomas, spinal cord injury, conditions of the central nervous system particularly diseases characterized by neuro-degeneration, and metabolic syndrome and its complications.

DETAILED DESCRIPTION OF THE INVENTION

Although a bipolar trans carotenoid (BTC) such as trans sodium crocetinate (TSC), is a member of the carotenoid family of compounds, it cannot be orally dosed in a manner similar to other carotenoids which are sold in capsule or pill form (e.g., beta carotene or Vitamin A). Two factors which must be accounted for in developing an oral formulation of a BTC compound are pH and solubility considerations which are totally different from other carotenoid compounds. Methods used for formulation of other carotenoid compounds simply don't work for compounds such as TSC.

TSC is precipitated under acidic conditions, such as those which exist in the stomach. This solid material is practically insoluble in the acidic environment of the stomach. TSC is not stable in acidic conditions and will be converted to the cis isomer which can precipitate. A system has been devised that will protect TSC in the harsh, acidic environment of the stomach and release TSC in a more favorable pH region. A more favorable pH does exist in the small intestines. In-situ closed loop studies have shown increased bioavailability when TSC is administered directly to the small intestine compared to the stomach. See Examples below. TSC's effectiveness is believed to be dependant on the TSC concentrations levels found in the body. The effectiveness of TSC can be prolonged by administering TSC orally.

Tablets of bipolar trans carotenoids include excipients that are commonly used in making tablets. Advantageously, tablets also have an enteric coating placed on them, so that they will dissolve in the higher pH ($>5.5$) areas of the digestive track instead of in the acidic stomach.

Figure 3:
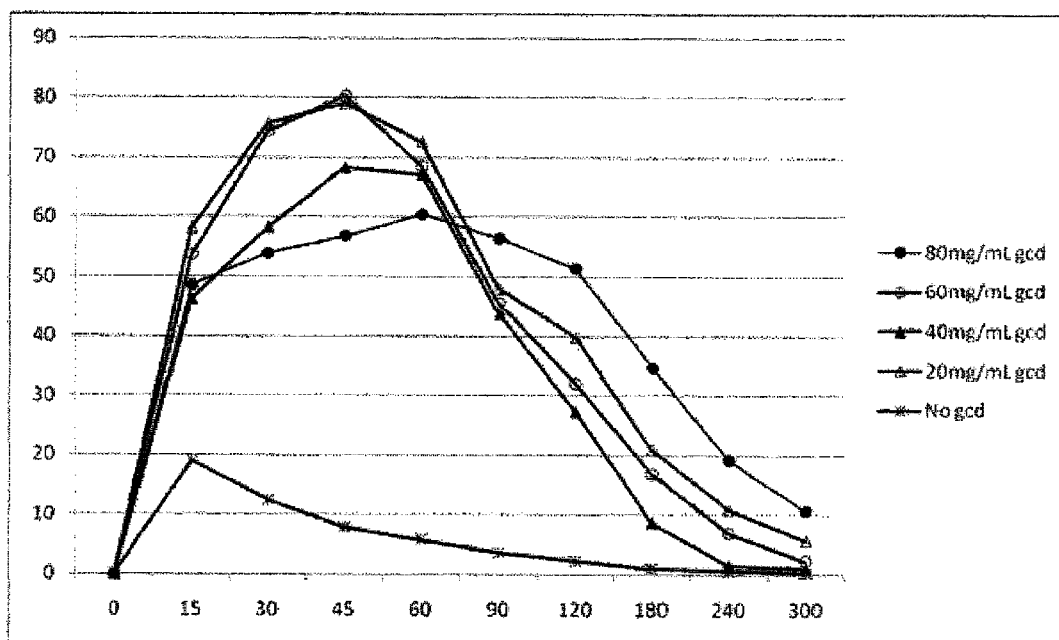

The FIG. 3 graph is TSC plasma concentration versus time following administration.

FIG. 4 shows the effect of TSC dosage in a TSC-γ-cyclodextrin mixture on Cmax.

Figure 5:
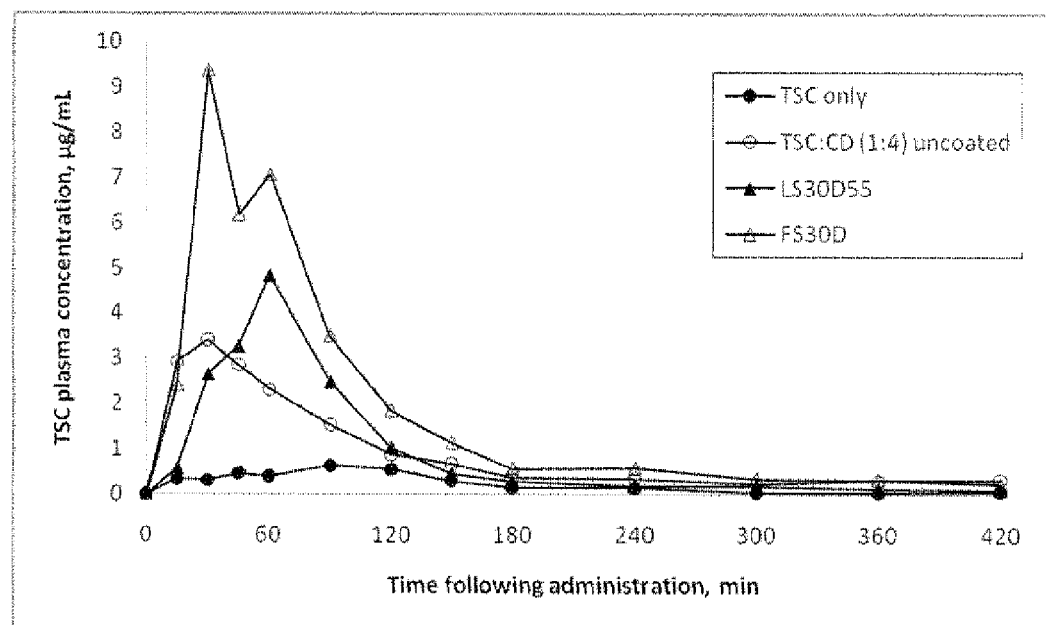

FIG. 5 shows the concentration in the blood stream after oral administration to rats.

Figure 6:
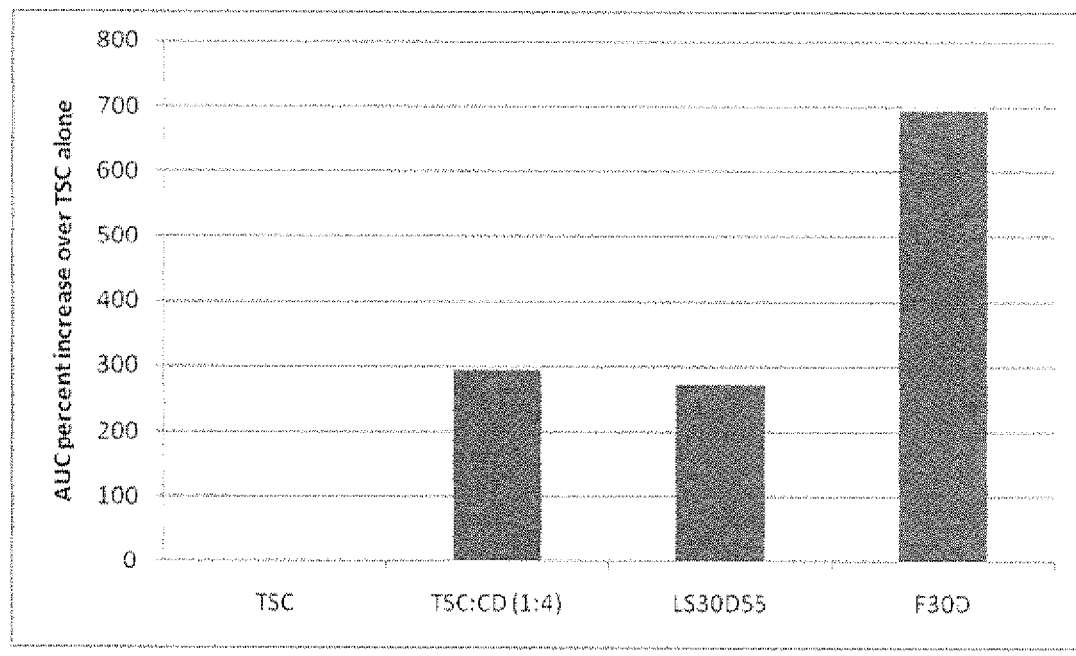

FIG. 6 shows the percentage improvement in absorption.

Figure 7:
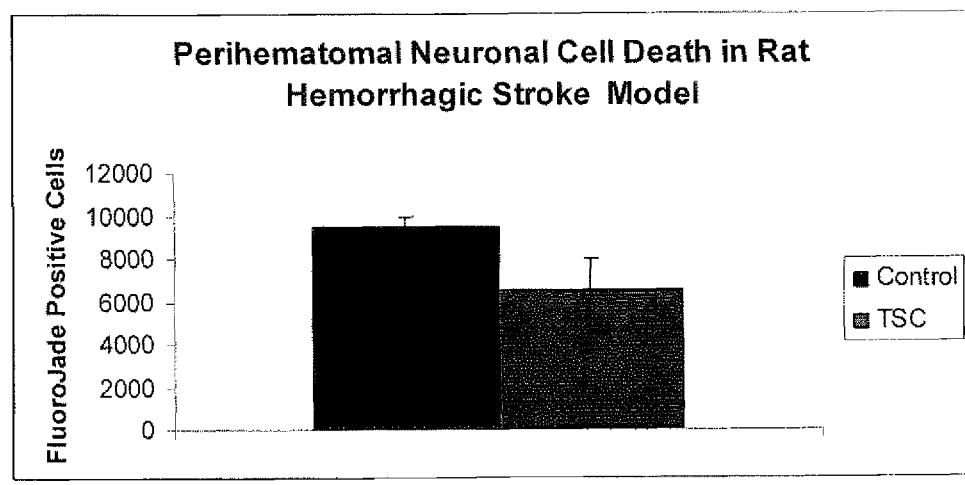

FIG. 7 shows less neuronal death in animals treated with TSC.

Figure 8:
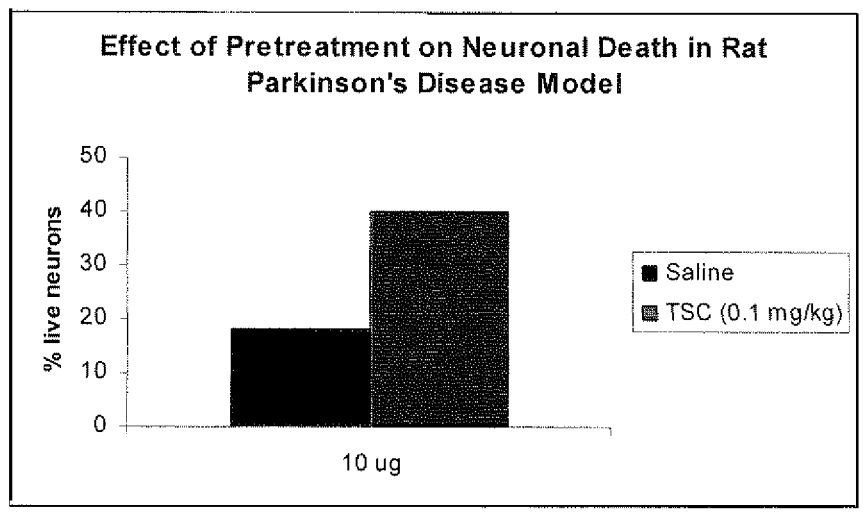

FIG. 8 shows the effect of TSC pretreatment on neuronal death in rats.

Figure 9:
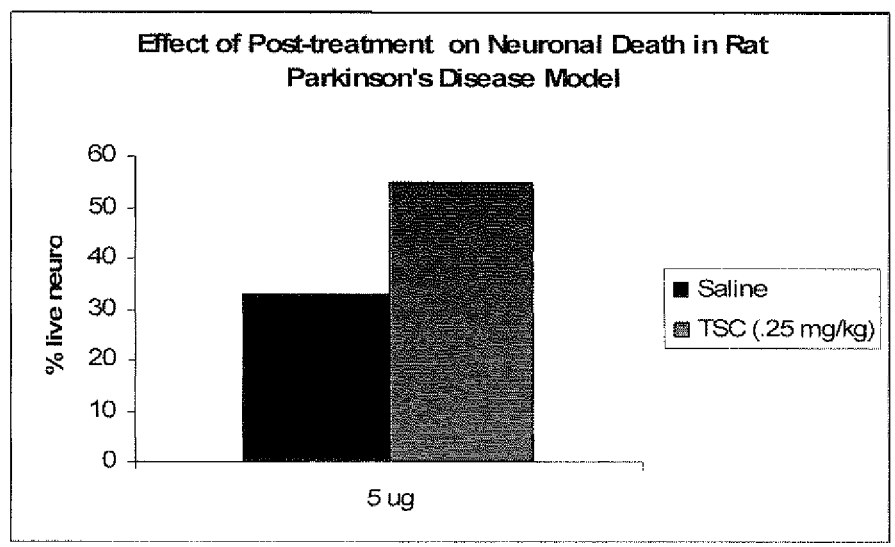

FIG. 9 shows the effect of TSC post-treatment on neuronal death in rats.

Figure 10:
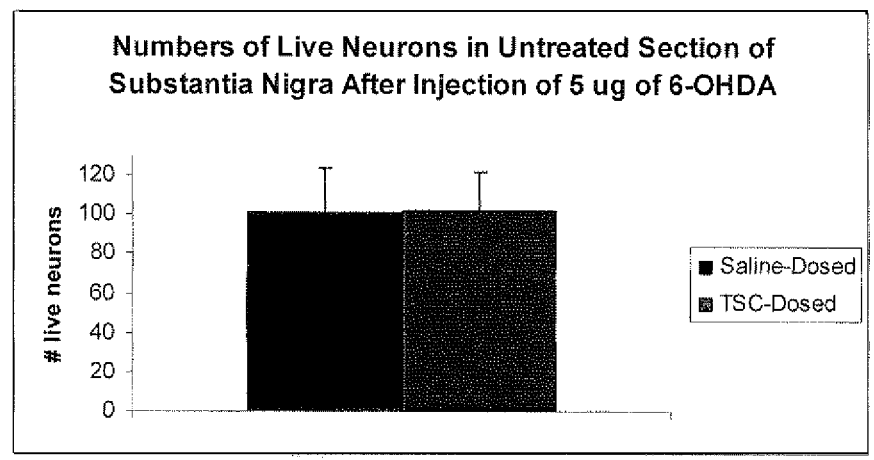

FIG. 10 shows that TSC has no effect on the viability of live neurons.

Figure 11:
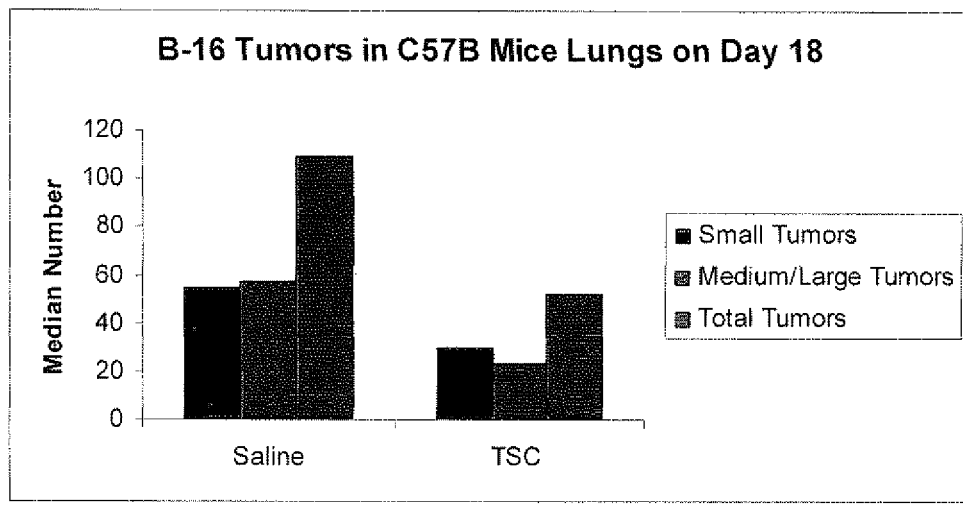

FIG. 11 shows data on B-16 Tumors in C57B Mice Lungs on Day 18 (median values).

Figure 12:
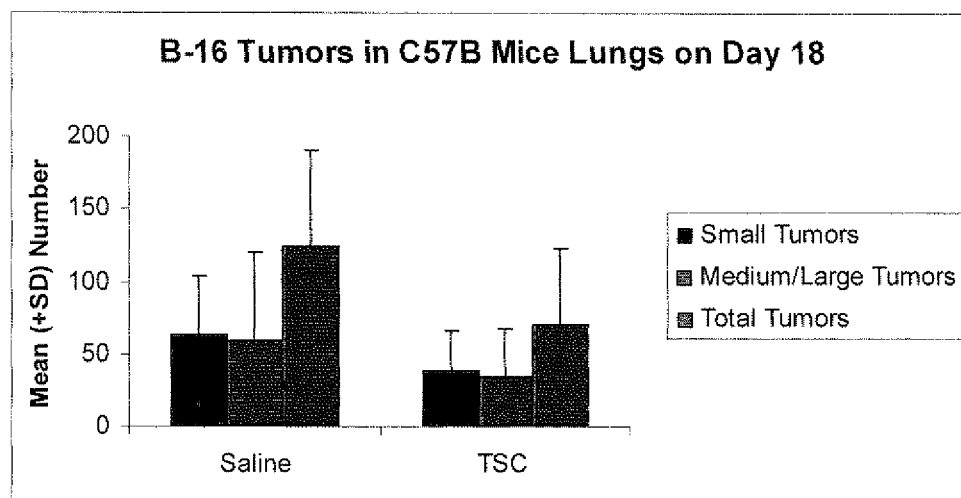

FIG. 12 shows data on B-16 Tumors in C57B Mice Lungs on Day 18 (mean values).

COMPOSITIONS OF THE INVENTION

The compositions of the subject invention are all manufactured to be pharmaceutical grade, i.e. pharmaceutical compositions. Such formulations can include pharmaceutically acceptable carriers known to those skilled in the art as well as other therapeutic agents. Advantageously, the formulation does not include a compound that inhibits the ability of the diffusing enhancing compound to improve diffusivity.

The compositions of the subject invention include a) a diffusion enhancing compound, b) a cyclodextrin and c) a coating. As an alternative, a pH responsive carrier (i.e. TSC is dispersed/held in a polymer matrix), or a time release system (also known as sustained release, controlled, etc.) can be used.

A. Diffusion Enhancing Compounds

The diffusion enhancing compounds of the invention include those compounds described in U.S. Ser. No. 10/647,132, U.S. Ser. No. 11/361,054, U.S. Ser. No. 12/081,236 and U.S. Ser. No. 12/289,713, each of which is hereby incorporated by reference in its entirety.

The diffusion enhancing compounds of the subject invention are trans carotenoids including trans carotenoid diesters, dialcohols, diketones and diacids, bipolar trans carotenoids (BTC), and bipolar trans carotenoid salts (BTCS). Included are bipolar trans carotenoid compounds having the formula:

YZ-TCRO-ZY where:
Y=a cation
Z=a polar group which is associated with the cation, and
TCRO=trans carotenoid skeleton,
such as TSC.

More specifically:

Y (which can be the same or different at the two ends)=H or a cation other than H, preferably $Na^+$ or $K^+$ or $Li^+$. Y is
  advantageously a monovalent metal ion. Y can also be an organic cation, e.g., $R_4N^+$, $R_3S^+$, where R is H, or $C_nH_{2n+1}$ where n is 1-10, advantageously 1-6. For example, R can be methyl, ethyl, propyl or butyl.

Z (which can be the same or different at the two ends) =polar group which is associated with H or the cation. Optionally including the terminal carbon on the carotenoid (or carotenoid related compound), this group can be a carboxyl ($COO^-$) group or a CO group (e.g. ester, aldehyde or ketone group), or a hydroxyl group. This group can also be a sulfate group ($OSO_3^-$) or a monophosphate group ($OPO_3^-$), ($OP(OH)O_2^-$), a diphosphate group, triphosphate or combinations thereof. This group can also be an ester group of COOR where the R is $C_nH_{2n+1}$.

TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups (X) are typically methyl groups but can be other groups as discussed below. In an advantageous embodiment, the units of the skeleton are joined in such a manner that their arrangement is reversed at the center of the molecule. The 4 single bonds that surround a carbon-carbon double bond all lie in the same plane. If the pendant groups are on the same side of the carbon-carbon double bond, the groups are designated as cis (also known as "Z"); if they are on the opposite side of the carbon-carbon bond, they are designated as trans (also known as "E"). Throughout this case, the isomers will be referred to as cis and trans.

The compounds of the subject invention are trans. The cis isomer typically is a detriment—and results in the diffusivity not being increased. In one embodiment, a cis isomer can be utilized where the skeleton remains linear. The placement of the pendant groups can be symmetric relative to the central point of the molecule or can be asymmetric so that the left side of the molecule does not look the same as the right side of the molecule either in terms of the type of pendant group or their spatial relationship with respect to the center carbon.

The pendant groups X (which can be the same or different) are hydrogen (H) atoms, or a linear or branched hydrocarbon group having 10 or less carbons, advantageously 4 or less, (optionally containing a halogen), or a halogen. X could also be an ester group (COO—) or an ethoxy/methoxy group. Examples of X are a methyl group ($CH_3$), an ethyl group ($C_2H_5$), a phenyl or single aromatic ring structure with or without pendant groups from the ring, a halogen-containing alkyl group (C1-C10) such as $CH_2Cl$, or a halogen such as Cl or Br or a methoxy ($OCH_3$) or ethoxy ($OCH_2CH_3$). The pendant groups can be the same or different but the pendant groups utilized must maintain the skeleton as linear.

Although many carotenoids exist in nature, carotenoid salts do not. Commonly-owned U.S. Pat. No. 6,060,511 hereby incorporated by reference in its entirety, relates to trans sodium crocetinate (TSC). The TSC was made by reacting naturally occurring saffron with sodium hydroxide followed by extractions that selected primarily for the trans isomer.

The presence of the cis and trans isomers of a carotenoid or carotenoid salt can be determined by looking at the ultraviolet-visible spectrum for the carotenoid sample dissolved in an aqueous solution. Given the spectrum, the value of the absorbance of the highest peak occurs in the visible wave length range of 380 to 470 nm (the number depending on the solvent used and the chain length of the BTC or BTCS). The addition of pendant groups or differing chain lengths may change this peak absorbance but someone skilled in the art will recognize the existence of an absorbance peak in the visible range corresponding to the conjugated backbone structure of these molecules, divided by the absorbency of the peak which occurs in the UV wave length range of 220 to 300 nm, can be used to determine the purity level of the trans isomer. When the trans carotenoid diester (TCD) or BTCS is dissolved in water, the highest visible wave length range peak will be at between 380 nm to 470 nm (depending on the exact chemical structure, backbone length and pendant groups) and the UV wave length range peak will be between 220 to 300 nm. According to M. Craw and C. Lambert, Photochemistry and Photobiology, Vol. 38 (2), 241-243 (1983) hereby incorporated by reference in its entirety, the result of the calculation (in that case crocetin was analyzed) was 3.1, which increased to 6.6 after purification.

Performing the Craw and Lambert analysis on the synthetic TSC as described in U.S. Ser. No. 10/647,132 and U.S. Ser. No. 11/361,054, that ratio is greater than 7.0 (e.g. 7.0 to 8.5), advantageously greater than 7.5 (e.g. 7.5-8.5), most advantageously greater than 8. The synthesized material is a "purer" or highly purified trans isomer.

Advantageously, the trans carotenoid is crocetin, crocin, a bipolar trans carotenoid (BTC) salt such as TSC, or a carotenoid diester, alcohol or acid.

B. Cyclodextrins

Many excipients have been suggested to increase bioavailability of drugs from the gastrointestinal tract such as surfactants, chelating agents, glycols, polyethylene glycol and others; however, cyclodextrin with a bipolar trans carotenoid works extremely well.

A detailed description of cyclodextrins in combination with bipolar trans carotenoids can be found in commonly owned application U.S. Ser. No. 11/361,054 which is hereby incorporated by reference in its entirety.

Advantageously, the bipolar trans carotenoid is in the form of a composition comprising a trans carotenoid and a cyclodextrin, for example alpha cyclodextrin, beta cyclodextrin or gamma cyclodextrin. The cyclodextrin can be hydroxylpropyl-beta-cyclodextrin or 2-hydroxylpropyl-gamma-cyclodextrin. In another embodiment, the composition further comprises mannitol or saline. In a still further embodiment, the composition further comprises a compound to regulate pH such as bicarbonate or glycine. Advantageously, the ratio of a bipolar trans carotenoid to the cyclodextrin is up to 1:10. Advantageously, up to 1:4, e.g. 2:1, 1:1, or 1:4.

C. Coatings

An enteric coating is a barrier applied to oral medication that controls the location in the digestive system where it is absorbed. Enteric refers to the small intestine, therefore enteric coatings prevent release of medication before it reaches the small intestine. Most enteric coatings work by presenting a surface that is stable at the highly acidic pH found in the stomach, but breaks down rapidly at a less acidic (relatively more basic) pH. For example, they will not dissolve in the acidic juices of the stomach (pH of 1 to 3), but they will in the higher pH(above pH 5.5) environment present in the small intestine. Materials used for enteric coatings include fatty acids, waxes, and shellac as well as plastics.

Bipolar trans carotenoids precipitate in acid conditions. For such types of drugs, an enteric coating can be added to the formulation to protect the active substance from the stomach's acidic exposure, delivering the active instead to a basic pH environment (intestine's pH 5.5 and above) where it is more soluble, and can give its desired action.

TSC's effectiveness is believed to be dependent on the TSC concentrations levels found in the body. The effectiveness of TSC can be prolonged by administering TSC orally. Since TSC precipitates in acidic conditions, the compositions of the subject invention protect TSC in the harsh, acidic environment of the stomach and release TSC in a more favorable pH region in the intestines.

An enteric coating is applied to oral dosage formulations in order to protect the active substance from dissolution in the gastric fluid within the stomach. The most common reasons for using an enteric coating include:
- Protection of the active substance from the gastric enzymes or acidity of the gastric fluid
- Masking of the task or odor
- Preventing irritation of the stomach including nausea and vomiting
- Sustained release for controlled absorption
- Delivery of the active substance to a specific site in the digestive tract that is more favorable for systemic absorption Another embodiment includes using an enteric coating that responds at a broader range of pH values in order to allow a bipolar trans carotenoid such as TSC to absorb in more sections of the intestines, thus increasing the surface area available for absorption.

Composition of Coatings

There are many materials available that are used to enterically coat materials. Most function by either a slow erosion of the coating material (carnauba wax, keratin, gluten, etc.) or by a pH responsive coating. Materials relying on the erosion mechanism are dependent on gastric emptying times. The second type, the pH responsive coating, are hydrophobic and water insoluble at low pH conditions and become soluble at higher pHs. Thus, the coating is insoluble at the harsh acidic environment of the stomach and dissolves at the higher pH region of the intestine. There are many pH sensitive polymers available which can be selected based on a specific pH at which disintegration should occur. The table below lists some of the most common pH sensitive polymers.

Common pH Sensitive Polymers Used for Enteric Coatings

| |
| --- |
| Cellulose acetate phthalate (CAP) |
| Cellulose acetate succinate |
| Acrylate polymers |
| Hydroxy propyl methyl cellulose phthalate |
| Hydroxy propyl methyl cellulose acetate succinate |
| Polyvinyl acetate phthalate |

Three commercially available acrylate polymers—copolymers derived from esters of acrylic and methacrylic acid are Eudragit L30D-55, L100, and FS30D. The pH-dependent functionality of these polymers are determined by their functional, carboxylic acid groups:

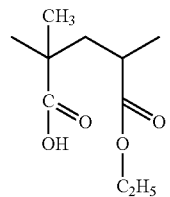

Eudragit L30D-55: Dissolution occurs at a pH of 5.5 or greater with a targeted release area of the duodenum.

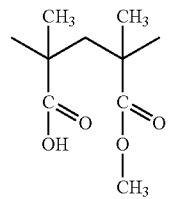

Eudragit L100: Dissolution occurs at a pH above 6.0 with a targeted release area of the jejunum.

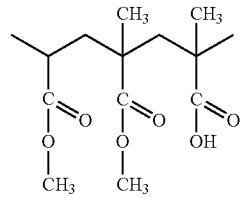

Eudragit FS30D: Dissolution occurs at a pH above 7.0 with a targeted release area of the colon.

D. Other Ingredients

Agents can be added to buffer the diffusion enhancing compounds. Other agents can be added to affect the osmolality, or added as compounding agents needed for oral formulations. Specific buffering agents include glycine, sodium carbonate, sodium bicarbonate, magnesium carbonate, and aluminum hydroxide. Specific agents to affect osmolality include mannitol, and polysaccharides.

Other agents that can be added include:

Prosolv 90 is a silicified microcrystalline cellulose. The PROSOLV SMCC 90 is said to offer a balance of best in class compaction and flow for tablet formulations. It improves formulation flow, enhances consolidation of the particles, and improves content uniformity.

Crospovidone XL 90 is a cross-linked polyvinylpyrrolidone which is used in tableting as a spheronization aid and an alternative to microcrystalline cellulose. Spheronization, marmumerization, pelletization and micropelletization all mean the same thing: the manufacture of products in small spheres for use in pharmaceutical and related industries. All the products produced by these processes can be called spheroids, spheres, micro-spheres, pellets, micro-pellets or pharmaceutical pellets. All these terms refer to the same thing. Size range is normally from about 0.8 mm to 1.5 mm in diameter although smaller and larger are possible. In contrast, the term granulation normally refers to irregularly shaped particles with a large size range within a batch. Granulated materials are generally less dense.

Magnesium stearate, also called octadecanoic acid, magnesium salt, is a white substance which is solid at room temperature. It has the chemical formula $C_{36}H_{70}MgO_4$. It is a salt containing two equivalents of stearate (the anion of stearic acid) and one magnesium cation ($Mg^{2+}$).

Magnesium stearate melts at about 88° C., is not soluble in water, and is generally considered safe for human consumption. Because it is widely regarded as harmless, it is often used as a filling agent in the manufacture of medical tablets and capsules. In this regard, the substance is also useful because it has lubricating properties, preventing ingredients from sticking to manufacturing equipment during the compression of chemical powders into solid tablets.

Kollidon is a polyvinyl polymer of variable molecular weight; used as a suspending and dispersing agent and vehicle for pharmaceuticals.

Methods of Formulation

Formulations of the present invention suitable for oral administration can be presented as discrete units such as pills, capsules, cachets or tablets, as powder or granules, or as a solution, suspension or emulsion. Formulations suitable for oral administration further include lozenges, and pastilles. The formulations can conveniently be presented in unit dosage form, and can be prepared by methods known in the art of pharmacy. The formulation can be for immediate, or slow or controlled release of the diffusion enhancing compound. The advantages of a sustained release system (also known as time release, controlled release, etc.) are that dosing frequency can decrease and the systemic drug concentrations are steadier for a longer duration as compared to other formulations of the same drug.

Appropriate dosages of the compositions of the invention will depend on the metabolism of the given compound, and the severity of the condition being treated. For a dose to be "therapeutically effective", it must have the desired effect, i.e. it must relieve symptoms of the indication for which it is given. The therapeutically effective dosage will depend upon the condition treated, the severity of the condition, the stage and individual characteristics of each mammalian patient addressed, and the clearance of the diffusion enhancing effect.

Typically the compositions of the invention are made by mixing the bipolar trans carotenoid and the selected cyclodextrin at a ratio of up to 1:10. Mixing is done by any pharmaceutically accepted method. The mixture is then either loaded into a capsule container or stamped into a tablet (which also can contain the ingredients mentioned previously to promote release from the molds, etc.). The capsules or tablets are then coated by pH-sensitive polymer such as a Eudragit in such a manner so as to create a continuous coating.

In one embodiment of the invention, multiple types of enterically coated beads are placed in a capsule or other system for oral delivery. The beads are composed of a first portion or group of beads having a first coating and a second portion or group of beads having a second coating. Additional groups of beads with different coatings can also be added. An example is a capsule containing beads having three different types of Eudragit coatings that release at different pH values and release over a longer period of time than a capsule containing only one type of bead.

Therapeutic Uses and Modes of Administration

The compositions of the invention have therapeutic uses in treating mammals having tissues experiencing low oxygen levels (hypoxia) or in various conditions involving the central nervous system.

The uses of the compositions of the invention include those disclosed in commonly owned U.S. Pat. No. 6,060,511, U.S. patent application Ser. No. 10/647,132, U.S. patent application Ser. No. 11/361,054, U.S. patent application Ser. No. 12/081,236 and U.S. provisional Patent application Ser. No. 61/213,575, each of which is hereby incorporated by reference in its entirety.

The oral compositions of the invention are useful in the treatment of:
- hemorrhagic shock,
- respiratory disease, asthma, emphysema, ALI, ARDS, COPD
- ischemic,
- cardiovascular disease, atherosclerosis, myocardial infarction, hypertension, ventricular fibrillation
- stroke, traumatic brain injury, cerebral edema,
- conditions of the central nervous system (Alzheimer's disease, Parkinson's disease, and other neurodegenerative diseases) Neurodegeneration is the umbrella term for the progressive loss of structure or function of neurons, including death of neurons. Examples of degenerative nerve diseases include: Alzheimer's disease, Parkinson's disease, amyotrophic lateral sclerosis, Friedreich's ataxia, Huntington's disease, Lewy body disease, and spinal muscular atrophy. See Example 7.
- arthritis,
- anemia, (anemia of prematurity, Fanconi anemia, hymolytic anemia, microcytic anemia, a normochromic anemia, a macrocytic anemia, hereditary spherocytosis, sickle-cell anemia, warm autoimmune hemolytic anemia, cold agglutinin hemolytic anemia),
- chronic renal failure, hypertension,
- papillomas, spinal cord injuries,
- cancer (advantageously as an adjunct to i) radiation therapy including external beam radiation, gamma knife, brachytherapy, tomotherapy, and proton beam, including fractionated, 3D conformal radiotherapy, intracavitary radiation, and intensity modulated radiotherapy (IMRT), and/or ii) chemotherapy including temozolimide).
- diabetes, diabetic retinopathy,
- peripheral vascular disease/claudication, embolism, blood clot, spinal stenosis/neurogenic claudication,
- diseases where organs do not get enough oxygen such as Wegener's granulomatosis The compositions of the invention are also useful as a pretreatment or for treating mammals at risk for the above-noted diseases/conditions.

The compositions are also useful in neuroprotection, i.e. in preventing or delaying the complications associated with neurodegenerative disorders such as Parkinsons disease or Alzheimers disease. They are also useful in reducing the amount of ischemia resulting from surgery in a mammal by administering the composition before during or after surgery The compositions are also useful in enhancing performance when respiration/exertion is increased or stressed, in increasing aerobic metabolism, and in increasing endurance during physical activity such as running walking or lifting.

For the following uses, the diffusion enhancing compounds are administered by any suitable route including oral, nasal or inhalation, topical, parenteral (including subcutaneous, intramuscular, intravenous, intradermal, transdermal and intraosseus), vaginal or rectal. The preferred route of administration will depend on the circumstances. An inhalation route, or intravenous or intramuscular injection is advantageous for treatment in emergency situations, where it is necessary for the diffusion enhancing compound to enter the bloodstream very quickly. In one embodiment, a composition of a cyclodextrin and bipolar trans carotenoid dissolved in sterile water can be injected, either intramuscularly (IM) or intravenously (IV). The formulations thus include those suitable for administration through such routes (liquid or powder to be nebulized). It will be appreciated that the preferred route may vary, for example, with the condition and age of the patient.

- critical limb ischemia
- Parkinson's disease, amyotrophic lateral sclerosis, Friedreich's ataxia, Huntington's disease, Lewy body disease, and spinal muscular atrophy,
- multiple sclerosis,
- metabolic syndrome
- peripheral neuropathy
- cerebral palsy
  - cancer—a bipolar trans carotenoid salt, such as TSC, is the chemotherapy used to cause regression of many types of cancerous tumors, i.e. without use of radiation or other chemotherapy. Example 8 relates to treating cancerous tumors with TSC. TSC does not work by killing the cancer cells, but, while not wishing to be bound by theory, is thought to work by causing the cells to revert to more mature (and thus, more nearly normal) cells. The use of retinoids (such as all trans retinoic acid), or their salts, for the treatment of cancer is excluded from the invention. Examples of the types of cancer/tumors which can be treated are: skin, lung, breast, brain, bladder, prostate and colon cancers/tumors.

In one embodiment, more than one diffusion enhancing compound is administered. Alternatively, hemoglobins or fluorocarbons and a diffusion enhancing compound can be given together.

The following Examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1

Tablet Composition (without Cyclodextrin)

Two formulations were made that consist of the following ingredients:

| 65% Blend | |
|---|---|
| 65.0% | TSC |
| 26.0% | Prosolv 90 |
| 2.9% | Crospovidone XL 90 |
| 1.5% | Magnesium Stearate |
| 4.6% | Kollidon |
| 60% Blend | |
| 60.4% | TSC |
| 30.1% | Prosolv 90 |
| 3.8% | Crospovidone XL 90 |
| 1.4% | Magnesium Stearate |
| 4.3% | Kollidon |

The TSC tablets were made in three (3) steps:

Step 1: A mixture containing 70% TSC, 25% Prosolv 90 and 5% Kollidon 25 were mixed in a bag for 5 minutes and roll compacted using a Vector roller compactor. The conditions for the roller compactor were roll pressure=800 psi, screw speed=10 rpm, roll speed=0.95 rpm. This produced a blend called TSC Blend I.

Step 2: The TSC Blend I from Step 1 was roll compacted using Crospovidone XL 10 and magnesium stearate. The percentages were 97.5% TSC Blend I, 2% Crospovidone XL 10 and 0.5% magnesium stearate. The product of this step is called TSC Granules II.

Step 3: The ribbons from Step 2 were hand crushed and sieved through 20 mesh screen. The granules obtained were mixed with excipients (see below) to get final blends containing 65% TSC and 60% TSC.

| 65% TSC Blend | 60% TSC Blend |
|---|---|
| 95.2% TSC Granules II | 88.5% TSC Granules II |
| 2.8% Prosolv 90 | 8.5% Prosolv 90 |
| 1% Crospovidone XL | 2% Crospovidone XL |
| 1% Magnesium Stearate | 1% Magnesium Stearate |

Step 4: The tablets were coated with CAP (cellulose acetate phthalate)

To demonstrate the difference in absorption in the stomach and in the intestine, the following studies were performed.

Example 2

Absorption of TSC Solutions

Male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

Following cannulation, animals were placed into one of two groups: administration of a TSC dosage formulation directly into the 1) stomach via gavage; or 2) into an isolated intestinal segment. For dosing into an isolated intestinal segment, a front midline in was made, exposing the abdomen and intestinal segments. In this study, the ileum was isolated and cannulated with PE-50 tubing, then washed with normal 37° C. saline until the washings run clear. The segment was replaced, the abdomen clamped, and the rat was allowed to stabilize for 1 hour. The TSC formulation was then introduced into the isolated segment. The intestine was replaced and the abdomen closed with sutures. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

Figure 1:
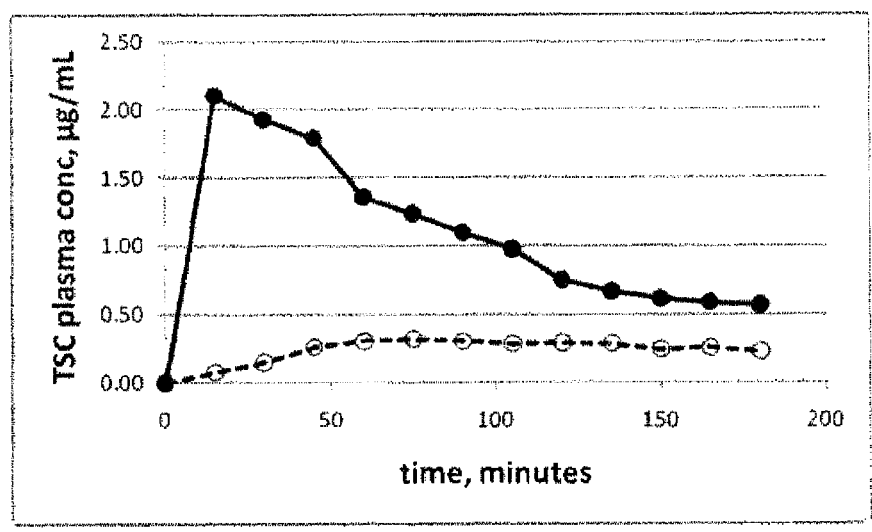
FIG. 1 shows increased bioavailability when TSC is administered directly to the small intestine as compared to the stomach.

The TSC dosage formulation administered in this study consisted of an intravenous formulation (20 mg/mL TSC, 8% gamma cyclodextrin, 50 mM Glycine, and 2.3% Mannitol). FIG. 1 shows that there is an increased bioavailability when TSC is administered directly to the small intestine as compared to the stomach.

Example 3

Enteric Coated Tablets (without Cyclodextrin)

TSC is precipitated and is practically insoluble under the harsh acidic environment of the stomach. TSC must be protected from the harsh environment of the stomach and be release in a more favorable, higher pH region of the small intestine. For this study, tablets of TSC were made (Table 1) and were enterically coated with either Eudragit L100 or cellulose acetate phthalate (CAP). The integrity of both types of protective coatings were confirmed in a USP dissolution study in which enterically coated tablets were first place in a dissolution cell containing simulated gastric fluid (SGF), then transferred to another cell containing simulated intestinal fluid (SIF). The coating and tablet remained intact in the SGF, but dissolution did occur in SIR. This study was performed according to USP protocols.

TABLE 1

| TSC tablet formulation | |
|---|---|
| 65% TSC Blend | 60% TSC Blend |
| 95.2% TSC Granules II | 88.5% TSC Granules II |
| 2.8% Prosolv 90 | 8.5% Prosolv 90 |
| 1% Crospovidone XL | 2% Crospovidone XL |
| 1% Magnesium Stearate | 1% Magnesium Stearate |

These tablets were made using tabletting technology known to one skilled in the art.

Then, in order to examine what happens with enterically-coated TSC, a tablet coated with CAP, and containing 300 mg TSC using the 65% blend, was administered orally to dogs. Very low plasma TSC concentrations were found, suggesting that the bioavailability would be too low for clinical use in this formulation.

Example 4

Intestinal Absorption of TSC and Effect of Cyclodextrin

Additional studies were conducted in order to determine the effect on systemic absorption with the addition of gamma cyclodextrin to the TSC.

Male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

Following cannulation, a front midline in was made, exposing the abdomen and intestinal segments. In this study, the jejunum was isolated and the TSC formulation was administered in the proximal jejunum. Approximately 60 mg/kg TSC was administered at various gamma cyclodextrin ratios of 0.5:1 up to 4:1 (wt. TSC:wt. gamma cyclodextrin). Movement of TSC within the intestinal segments was not restricted distal to the site of administration. The intestine was replaced and the abdomen closed with sutures. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

Figure 2:
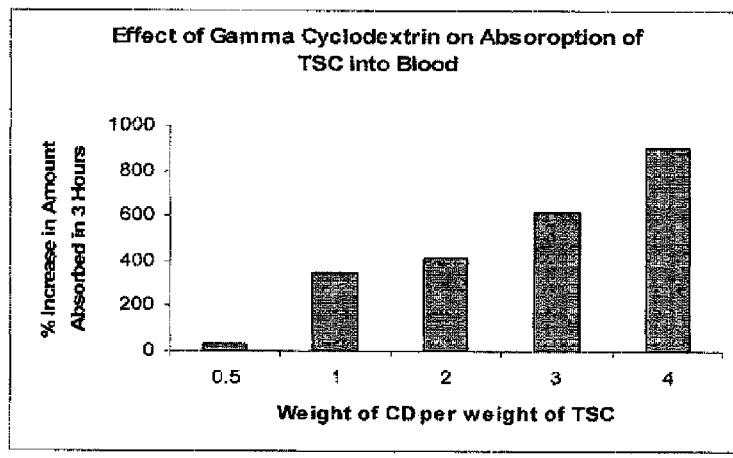
FIG. 2 shows the effect of g-cyclodextrin on TSC absorption in the jejunum of the rat.

It was found that the γ-cyclodextrin greatly enhances the absorption of the TSC as shown in FIG. 2.

FIG. 3 shows the pk curves following in-situ TSC administration into the small intestine. The curves show that cyclodextrin significantly increases intestinal absorption of TSC.

The FIG. 3 graph is TSC plasma concentration (µg/mL) vs. time following administration (min).

Example 5

Scalability for Cmax

It has been found that gamma cyclodextrin greatly enhances the systemic absorption of TSC in the GI tract. The dosage of TSC used in the above study is large, therefore, additional doses of TSC were administered with gamma cyclodextrin at a ratio of 1:1 (wt. TSC:wt. gamma cyclodextrin) in order to determine the scalability of systemic absorption (in terms of Cmax) with respect to TSC dosing amount. For the following study, TSC was administered to the jejunum intestinal segment at the following dosages: 2.5, 5, 10, and 60 mg/kg.

For this study, male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

Following cannulation, a front midline in was made, exposing the abdomen and intestinal segments. In this study, the jejunum was isolated and the TSC formulation was administered in the proximal jejunum. Movement of TSC within the intestinal segments was not restricted distal to the site of administration. The intestine was replaced and the abdomen closed with sutures. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

The results are shown in FIG. 4. The line in FIG. 4 is a linear regression of the data and shows that an excellent fit is obtained. This suggests that the data obtained for the inclusion of γ-cyclodextrin is scalable to other TSC dosages.

Example 6

Intestinal Absorption with and without Enteric Coatings

Additional studies were conducted in order to investigate the benefit of including gamma cyclodextrin with TSC for use in peroral delivery, For this study, TSC and gamma cyclodextrin at a ratio of 1:4 (wt TSC:wt. gamma cyclodextrin) were packed in size 9 gelatin capsules and either: 1) left uncoated, 2) enterically coated with Eudragit L30D-55 (also referred to as LS30D55 herein) (a coating which should disintegrate at a pH greater than 5.5), or 3) enterically coated with Eudragit. FS30D (a coating which should disintegrate at a pH greater than 7). Uncoated capsules containing TSC only (without cyclodextrin) were also administered.

For this study, male Sprague-Dawley (SD) and Wistar rats weighing approximately 300-400 g each were fasted for 24 hours prior to each experiment. Water was given ad libitum and coprophagy was prevented by using cages with wire-mesh floors. Anesthesia was induced and maintained with isoflurane. The carotid artery was exposed and cannulated with PE-50 tubing. The cannula was secured using silk sutures and 2% lidocaine was applied to the wound.

After cannulation, a gelatin capsule contain drug product was administered to the stomach via dosing syringe (Torpac, Fairfield N.J.) followed by 0.3 mL sterile water to the stomach via gavage. Approximately 0.3 mL blood samples were taken for the carotid artery at discrete time intervals following TSC administration. A small amount of sodium heparin was used as an anticoagulant. The blood samples were centrifuged and the resulting plasma volume mixed with 3 volumes of methanol and vortexed. The plasma mixture was then centrifuged and the supernatant was analyzed by HPLC to determine TSC levels.

The graph in FIG. 5 shows the concentration in the blood stream after oral administration to rats over a period of 7 hours of dry powders contained in gelatin capsules, with all capsules containing the same amount of TSC (about 4 mg).

TSC only shows the TSC alone in a capsule;

TSC:CD (1:4) uncoated, which is for capsules made of a 1 to 4 mixture of TSC to cyclodextrin but with no coating applied to the gelatin capsules;

LS30D55 which is for the same 1:4 capsule coated with Eudragit LS30D55 (a coating which should disintegrate at a pH greater than 5.5);

FS30D, which is for the same 1:4 capsule coated with Eudragit FS30D (a coating which should disintegrate at a pH greater than 7).

The bar graph in FIG. 6 shows the percentage improvement in absorption (as compared to TSC only) that is obtained with the uncoated capsules as well as the ones coated with the Eudragits.

Example 7

Neurodegenerative Disease

A major aspect of any neurodegenerative disease is, as stated above, the death of neurons. Studies have been conducted to look at the effects of TSC on neuronal death in different animal models.

The first study in which this was done was one conducted using a rat model of hemorrhagic stroke. For that study, the enzyme collagenase was injected through a burr hole in the skull into the right basal ganglion, which resulted in some of the brain blood vessels rupturing and bleeding out. TSC was then injected starting 3 hours after the collagenase was administered, and the animals were sacrificed 48 hours after the administration of the collagenase.

When there is a hemorrhage in the brain, the blood pools and forms a hematoma. Around the periphery of this hematoma, there is a death of neuronal cells. However, it was found that treating with TSC resulted in about 20% less death of the neurons. Use of the stain, fluorojade, allows one to count the numbers of "dead" neurons in a given brain section of the brain. This was done in the area around the hematomas formed in the hemorrhagic stroke rat model. It was found that there was approximately 30% less neuronal death in the animals treated with TSC as shown in the FIG. 7 graph.

Another model that was used examined the effect of TSC on neuronal viability is a rat model of Parkinson's disease. In this model, a burr hole is drilled through the skull and into the region of the substantia nigra. The Parkinson's-like condition is induced by injecting 6-hydroxydopamine (6-OHDA) into the brain. An amount of 10 □g of 6-OHDA is frequently injected in this model, and was used in the first study.

The first study with this model was designed to mimic a study found in the literature, in which pretreatment with crocetin was found to have a beneficial effect on neuronal death following the injection of 10 □g of 6-OHDA. In the study, TSC was injected at a dosage of 0.1 mg/kg for 7 days preceding the injection of the 6-OHDA (the same dosing regimen as had been done in the crocetin study). Following the injection of the 6-OHDA, no further treatments were given over the next 4 weeks.

At that time the rats were sacrificed and the brains removed and sent to Charles River Laboratories for counts of live neurons. This resulted in counts on the right side of the brain, where the 6-OHDA had been injected, as well as on the untreated left side of the brain. This allowed the comparison of cell death (treated side count/untreated side count) of the controls, which had been pretreated with saline, to the animals pretreated with TSC. The graph FIG. 8 shows these results.

As can be seen, the percentage of live neurons after this treatment is approximately doubled. It should also be noted that this is a very severe model of neuronal death, in that around 85% of the neurons are dead in the controls.

It is of much more interest to know the effect of post-treatment on neuronal death following the injection of 6-OHDA. To investigate that, 5 □g of 6-OHDA were again injected into the substantia nigra as before, but the treatment began following that injection. The animals were then given daily injections of TSC (0.25 mg/kg) for 4 weeks before sacrifice. The brains were removed and sent to Charles River Laboratories for neuronal counts.

As seen in FIG. 9, there are more live neurons (about 20% more) with the TSC treatment, and these data are statistically-significantly different ($p<0.05$).

An interesting result of this study was that the brain sections of the non-6-OHDA side of the brains showed almost the same numbers of live neurons regardless of whether saline or TSC were injected, as shown in the FIG. 10 graph. This demonstrates that TSC has no effect on the viability of live neurons.

These results, combined with those found in the hemorrhagic stroke model, teach that TSC exerts a neuroprotective effect in the brain.

Example 8

Chemotherapy with TSC

The pulmonary metastasis mouse model is a widely used model for the evaluation of tumor therapy. With B16 (mouse melanoma) cells, essentially all cells "take" upon intravenous cell injection in the tail vein, and the tumors are preferentially formed in the lungs. Thus, the term pulmonary metastasis is widely used even though every resulting pulmonary nodule is technically an independent "primary" tumor rather than a true metastasis.

Since the melanin in B16 cells does not bleach like the rest of the pulmonary tissues, the tumor nodules can be easily visualized after bleaching the extracted lungs in Fekete's solution. There is always a fraction of nodules that is amelanotic ("white") though, and this requires careful counting in order not to underestimate the tumor burden.

For the subject studies, eight-week-old female C57BL/6 mice were obtained from Charles River Laboratories. The mice were housed in groups of 5 or fewer, and received food and water ab libitum.

B16 cells were cultured by the Center for Cell Signaling of the University of Virginia using a standard protocol. The cells were received while they were in an exponential growth phase. The cells were supplied at a concentration of $5 \times 10^5$ cells/mL in Hank's buffered salt solution (HBSS).

The cells were injected immediately upon receipt, and this day was designated as Day 0. On Day 0, all of the mice were injected intravenously in the tail vein with 0.1 mL of the cell suspension, meaning that each mouse received $0.5 \times 10^5$ cells. The mice were then left alone until Day 4.

On Day 4, the mice were divided into two groups: Group A, consisting of 5 mice, received an intravenous injection of 0.05 mL of saline in the tail vein. Group B, composed of 7 mice, received an intravenous injection of 0.05 mL of a TSC solution in the tail vein, for a TSC dosage of 0.142 mg/kg/day. The same injections were repeated on Days 5-8 and on Days 11-15. On Day 18, the mice were sacrificed using carbon dioxide. The lungs were excised, rinsed and placed in Fekete's Solution and stored at room temperature.

Later, the lungs were assessed visually, in random, blinded order, to obtain a visual count of the numbers of tumors. It was found that there was a mixture of small tumors plus medium-sized and larger tumors. Thus, the tumors were counted visually in two separate groups: small tumors and medium/large tumors. Although the majority of the tumors were black, there were also some white tumors.

The results of the tumor counts are shown in the table and in the FIGS. 11-12 graphs. The table shows the median (med.) numbers of each type of tumor group as well as the mean±standard deviation. The FIG. 11 graph shows the median values and the FIG. 12 graph shows the mean values. The groups were not statistically different due to the large standard deviations.

TABLE

| Group | N | Small | | Medium/Large | | Total | |
|---|---|---|---|---|---|---|---|
| | | med. | mean | med. | mean | med. | mean |
| Saline | 5 | 55 | 64 ± 40 | 57 | 60 + 27 | 109 | 124 ± 66 |
| TSC | 7 | 18 | 32 ± 29 | 19 | 30 + 24 | 34 | 62 ± 53 |

It will be readily apparent to those skilled in the art that numerous modifications and additions can be made to both the present compounds and compositions, and the related methods without departing from the invention disclosed.

What is claimed is:

1. A method of increasing the diffusivity of oxygen in a mammal comprising administering orally to a mammal a therapeutically effective amount of a pharmaceutical composition comprising:

i) a bipolar trans carotenoid salt having the structure:

YZ-TCRO-ZY where
Y=a cation which can be the same or different,
Z=a polar group which can be the same or different and which is associated with the cation, and
TCRO=a linear transcarotenoid skeleton with conjugated carbon-carbon double bonds and single bonds and having pendant groups X, wherein the pendant groups X which can be the same or different, are (1) a linear or branched hydrocarbon group having 10 or less carbon atoms, or (2) a halogen, ii) a cyclodextrin, and iii) a coating that avoids conversion of the bipolar trans carotenoid to a cis isomer under acid conditions in a stomach of a mammal.

2. A method of treating a mammal having a disease or condition characterized by hypoxia comprising administering orally to such mammal a therapeutically effective amount of a pharmaceutical composition comprising:

i) a bipolar trans carotenoid salt having the structure:

YZ-TCRO-ZY where
Y=a cation which can be the same or different,
Z=a polar group which can be the same or different and which is associated with the cation, and
TCRO=a linear transcarotenoid skeleton with conjugated carbon-carbon double bonds and single bonds and having pendant groups X, wherein the pendant groups X which can be the same or different, are (1) a linear or branched hydrocarbon group having 10 or less carbon atoms, or (2) a halogen, ii) a cyclodextrin, and iii) a coating that avoids conversion of the bipolar trans carotenoid to a cis isomer under acid conditions in a stomach of a mammal.

3. A method of treating a mammal at risk of a disease or condition characterized by hypoxia comprising administering orally to such mammal a therapeutically effective amount of a pharmaceutical composition comprising:

i) a bipolar trans carotenoid salt having the structure:

YZ-TCRO-ZY where
Y=a cation which can be the same or different,
Z=a polar group which can be the same or different and which is associated with the cation, and
TCRO=a linear transcarotenoid skeleton with conjugated carbon-carbon double bonds and single bonds and having pendant groups X, wherein the pendant groups X which can be the same or different, are (1) a linear or branched hydrocarbon group having 10 or less carbon atoms, or (2) a halogen, ii) a cyclodextrin, and iii) a coating that avoids conversion of the bipolar trans carotenoid to a cis isomer under acid conditions in a stomach of a mammal.

4. A method as in claim 2 or 3 wherein said disease or condition characterized by hypoxia is selected from the group consisting of ischemia, cancer, traumatic brain injury, respiratory disease, hemorrhagic shock, cardiovascular disease, multiple organ failure, atherosclerosis, PAD, PVD, myocardial infarction, emphysema, asthma, ALI, ARDS, COPD, hypertension, cerebral edema, papillomas, spinal cord injury, stroke, and conditions of the central nervous system.

5. A method of treating a mammal having metabolic syndrome comprising administering to such mammal a therapeutically effective amount of a pharmaceutical composition comprising a bipolar trans carotenoid salt having the structure:

YZ-TCRO-ZY where
- Y=a cation which can be the same or different,
- Z=a polar group which can be the same or different and which is associated with the cation, and
- TCRO=a linear transcarotenoid skeleton with conjugated carbon-carbon double bonds and single bonds and having pendant groups X, wherein the pendant groups X which can be the same or different, are (1) a linear or branched hydrocarbon group having 10 or less carbon atoms, or (2) a halogen.

6. A method of treating a mammal having a neurodegenerative disease selected from the group consisting of Parkinson's disease, amyotrophic lateral sclerosis, Friedreich's ataxia, Huntington's disease, Lewy body disease, and spinal muscular atrophy, comprising administering to such mammal a therapeutically effective amount of a pharmaceutical composition comprising a bipolar trans carotenoid salt having the structure:

YZ-TCRO-ZY where
- Y=a cation which can be the same or different,
- Z=a polar group which can be the same or different and which is associated with the cation, and
- TCRO=a linear transcarotenoid skeleton with conjugated carbon-carbon double bonds and single bonds and having pendant groups X, wherein the pendant groups X which can be the same or different, are (1) a linear or branched hydrocarbon group having 10 or less carbon atoms, or (2) a halogen.

7. A method as in claim 5 or 6 wherein the bipolar trans carotenoid salt is TSC.

8. A method as in claim 5 or 6 wherein the pharmaceutical composition further comprises a cyclodextrin.

9. A method as in claim 5 or 6 wherein the pharmaceutical composition further comprises a cyclodextrin and a coating, and is administered orally.

10. A method as in claim 1 or 2, wherein the bipolar trans carotenoid salt is TSC.

11. A method as in claim 1 or 2, wherein the bipolar trans carotenoid salt is TSC, the cyclodextrin is gamma cyclodextrin, and the coating is an acrylate polymer.

12. A method as in claim 1 or 2, wherein the coating is an enteric coating.

13. A method as in claim 1 or 2, wherein the coating is an enteric coating which will release the bipolar trans carotenoid at pH greater than 5.5.

14. A method as in claim 1 or 2, wherein the coating is an enteric coating which will release the bipolar trans carotenoid at pH greater than 6.5.

15. A method as in claim 1 or 2, wherein the coating is a coating which will release the bipolar trans carotenoid in the intestines.

16. A method as in claim 1 or 2, wherein the coating is an acrylate polymer.

17. A method as in claim 1 or 2, wherein the cyclodextrin is selected from the group consisting of alpha cyclodextrin, beta cyclodextrin, and gamma cyclodextrin.

18. A method as in claim 1 or 2, wherein the bipolar trans carotenoid salt is synthetic trans sodium crocetinate wherein the purity level of the trans isomer in the composition is such that under UV-visible analysis, the absorbency of the highest peak which occurs in the visible wave length range divided by the absorbency of the peak which occurs in the UV wave length range is greater than 7.5.

19. A method as in claim 1 or 2, wherein said composition is in unit dosage form.

20. A method as in claim 1 or 2, wherein the composition is in the form of a tablet, pill, or capsule.

* * * * *